United States Patent [19]

Kikuchi

[11] Patent Number: 4,931,867

[45] Date of Patent: Jun. 5, 1990

[54] ELECTRONIC ENDOSCOPE APPARATUS HAVING AN ISOLATION CIRCUIT FOR ISOLATING A PATIENT CIRCUIT FROM A SECONDARY CIRCUIT

[75] Inventor: Kenichi Kikuchi, Hachioji, Japan

[73] Assignee: Olympus Optical Co., Ltd., Tokyo, Japan

[21] Appl. No.: 316,906

[22] Filed: Feb. 28, 1989

[30] Foreign Application Priority Data

Mar. 1, 1988 [JP] Japan .................................. 63-48364
Jun. 13, 1988 [JP] Japan ................................ 63-146644
Jan. 10, 1989 [JP] Japan ...................................... 1-3350

[51] Int. Cl.⁵ .............................................. A61B 1/04
[52] U.S. Cl. ....................................................... 358/98
[58] Field of Search ........................... 358/98, 93, 100; 128/4-6

[56] References Cited

U.S. PATENT DOCUMENTS 4,816,909 3/1989 Kimura et al. ......................... 358/98

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

The electronic endoscope apparatus having an isolation circuit of the present invention is provided with an endoscope provided with an imaging device converting the photoinformation of an object to an electric signal and a video signal processing device processing the output signal of the imaging device to be a video signal. An isolation circuit separates and isolates the circuit forming the video signal processing device into a patient circuit including the imaging device and a secondary circuit which is a circuit not included in the patient circuit. A signal producing circuit makes either one of the patient circuit and secondary circuit a transmitted side circuit and produces a signal required by the transmitted side circuit on the basis of a signal forming a video transmitted to the transmitted side circuit through the isolation circuit from the transmitting side circuit.

17 Claims, 11 Drawing Sheets

(a) LUMINANCE SIGNAL Y (b) COLOR DIFFERENCE SIGNAL R-Y/B-Y (c) OUTPUT (COLOR DIFFERENCE SIGNAL) OF 1/2 HDL 181

(d) OUTPUT OF ADDER 161

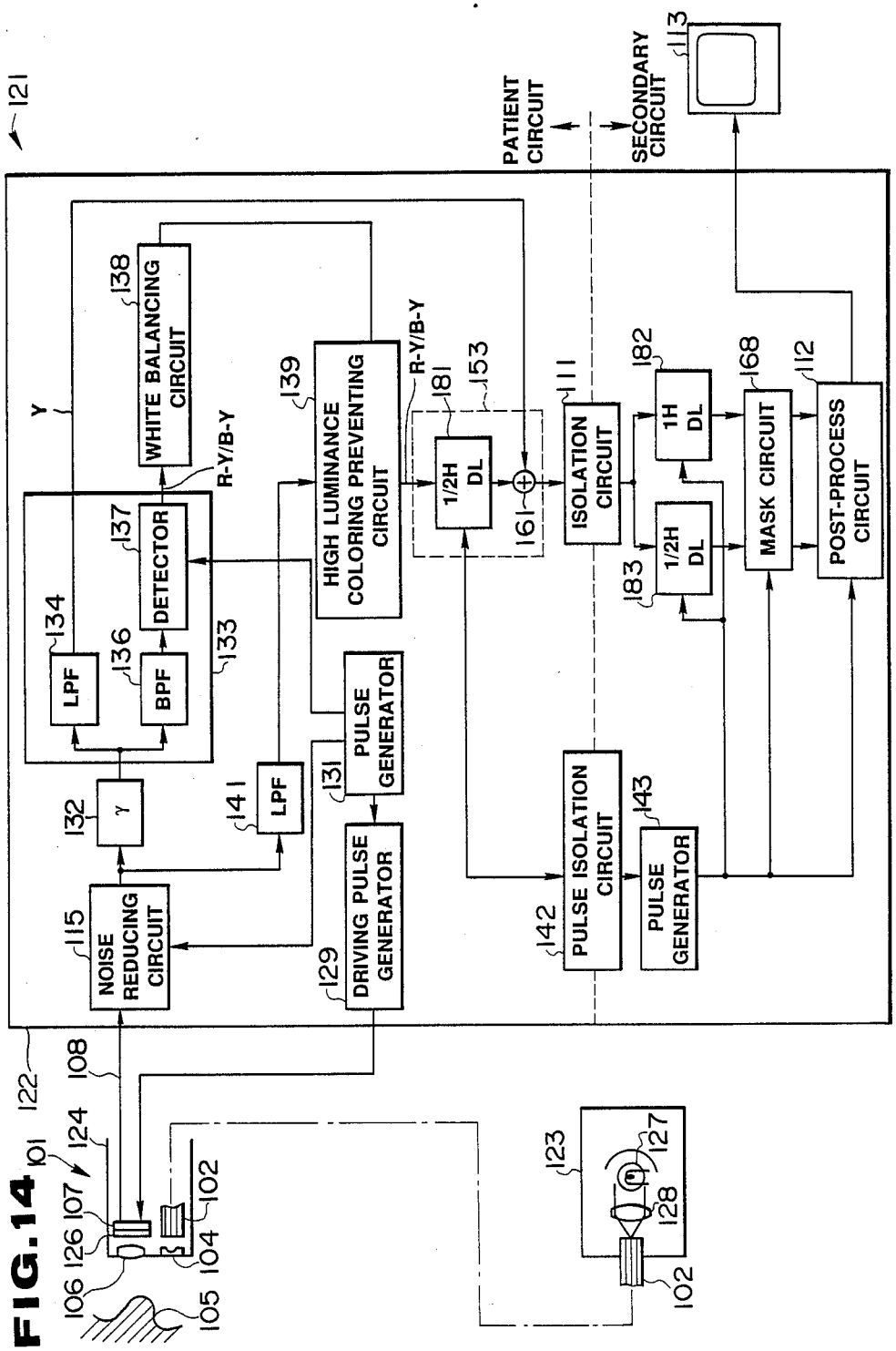

ELECTRONIC ENDOSCOPE APPARATUS HAVING AN ISOLATION CIRCUIT FOR ISOLATING A PATIENT CIRCUIT FROM A SECONDARY CIRCUIT

FIELD AND BACKGROUND OF THE INVENTION

This invention relates to an electronic endoscope apparatus wherein a patient circuit side and a secondary circuit side are isolated from each other.

Recently, there is extensively used an endoscope whereby an elongate insertable part is inserted into a body cavity to observe organs within the body cavity or, as required, various therapeutic treatments can be made by using a treating instrument inserted through a treating instrument channel.

There are also suggested various electronic endoscopes of a system wherein a solid state imaging device, such as a charge coupled device (CCD), is provided as an imaging means in the tip part of an insertable part and picture image information is taken out as a photoelectrically converted signal.

Now, in the case of a medical electronic endoscope, a circuit part (patient circuit) inserted into the body of a patient and a circuit part (secondary circuit) connected to a peripheral device such as a motor must be isolated from each other to prevent electrification.

FIGS. 1 to 3 show formation examples of such an electronic endoscope apparatus.

In FIG. 1, an image of an object 1 is formed on a solid state imaging device 3 by an image forming optical system 2 and a signal photoelectrically converted by this solid state imaging device 3 is transmitted to a video signal processing circuit 5 through a cable 4.

As this video signal processing circuit 5 is connected with a peripheral device such as a motor, the video signal is required to be isolated on the patient circuit side and secondary circuit side by an isolation circuit 6 within the video signal processing circuit 5.

In FIG. 2, an illuminating light output from a light source device (not illustrated) is led to a tip part 13 through a light guide 12 inserted through an electronic scope 11 and is radiated on to an object 15 through a light distributing lens system 14. The object 15 imaged by this illuminating light is formed on a CCD 17 by an image forming optical system 16. The signal photoelectrically converted by this CCD 17 is delivered to a pre-process circuit 20 forming a video signal processing circuit 19 through a signal transmitting cable 18, is pre-processed by this pre-process circuit 20, has a patient circuit and secondary circuit isolated from each other by an isolation circuit 21, is processed as determined by a post-process circuit 22, is output as a video signal as, for example, of an NTSC or three primary color signals of R, G and B and is displayed as an image by a color monitor 23 or the like.

The formation of the pre-process circuit 20 is shown in FIG. 3.

The output of the CCD 17 is amplified by an amplifier 24 to supplement the attenuation in the cable transmission and the attenuation for matching. The noise contained in the output of the CCD 17 is reduced by a noise reducing circuit 25 such as a correlated double sampler. A luminance signal Y and color difference signals R−Y and B−Y are generated by a luminance color reproducing circuit 26. These luminance signal Y and color difference signals R−Y and B−Y are input into the isolation circuit 21 and are transmitted from the patient circuit to the secondary circuit.

Now, particularly, in FIG. 2, three systems of transmitting lines are required in order to pass the luminance signal Y and color difference signals R−Y and B−Y through the isolation circuit. However, as the isolation circuit 21 must stably pass a high frequency signal and is expensive, if it is provided in each of the three systems, the cost will increase. Therefore, in order to reduce the cost, it is necessary to reduce the number of transmitting lines.

It may be possible isolate the circuits at a point forward of the luminance signal reproducing circuit 26. However, if the isolation between the patient circuit and secondary circuit is made forward of the circuit 26 the high frequency CCD 17 driving pulse, color demodulating pulse and correlated double sampling pulse will have to be transmitted through the isolation circuit. However, in the transformer used as the isolation circuit, as the high frequency component attenuates, no positive sampling will be made. If the phase of the color demodulating pulse slips, the color signal level will be reduced and, if the phase of the correlated double sampling pulse slips, the S/N of the video signal will be deteriorated. Therefore, for the above mentioned reasons, in case a high frequency pulse is passed through the isolation circuit, due to the delaying characteristic dispersion and temperature fluctuation, the picture quality will likely be deteriorated.

Particularly, when transmitting a timing pulse from the patient circuit side to the secondary circuit side, the reference clock will be of a high frequency usually above ten or more MH, and therefore a high frequency transformer or high speed photocoupler satisfying this band will be required for the isolation device.

Between the patient circuit side and the secondary circuit side, the isolation pressure-proofness is required to be high to meet the safety standard.

Therefore, a large expensive transformer or an expensive photocoupler having no space in the pressure-proofness must be used.

OBJECT AND SUMMARY OF THE INVENTION

An object of the present invention is to provide an electronic endoscope apparatus wherein the number of isolation circuits can be reduced, an expensive high frequency transformer or high speed photocoupler is not required to be used for the isolation circuit, the cost is low and the picture quality is not deteriorated.

The electronic endoscope apparatus having an isolation circuit of the present invention comprises an endoscope provided with an imaging device converting the photoinformation of an object into an output electric signal. A video signal processes device processing the output signal of the imaging device to be a video signal. An isolation circuit separates and isolates the circuit forming the video signal processing circuit into a patient circuit including the imaging device and a secondary circuit which is a circuit not included in the patient circuit. A signal producing circuit makes either one of the patient circuit and secondary circuit a transmitted side circuit and produces, based on the signal forming the video transmitted to the transmitted side circuit through the isolation circuit from the transmitting side circuit, a signal required by the transmitted side.

BRIEF DESCRIPTION OF THE DRAWINGS

FIG. 1 is a block diagram showing a formation example of an electronic endoscope.

FIG. 2 is a block diagram showing a formation example of another electronic endoscope.

FIG. 3 is a block diagram for explaining the formation of a pre-process circuit.

FIG. 4 is an explanatory view showing the entire electronic endoscope apparatus.

FIG. 6 is a block diagram showing the formation of an electronic endoscope apparatus for comparison with FIG. 5.

FIG. 8 is a block diagram for explaining the formation of an electronic endoscope apparatus.

FIG. 9 is an explanatory view of the formation of a color filter array.

FIG. 10 is a block diagram for explaining the formation of an electronic endoscope apparatus.

FIG. 11 is a timing chart view for explaining the operation of the electronic endoscope apparatus.

FIG. 12 is an explanatory view of a displayed picture image of a monitor.

FIGS. 14 and 15 relate to the fifth embodiment of the present invention.

FIG. 14 is a block diagram of an endoscope apparatus.

FIG. 15 is a timing chart view for explaining the operation of the endoscope apparatus.

DETAILED DESCRIPTION OF PREFERRED EMBODIMENTS OF THE INVENTION

Figure 1:
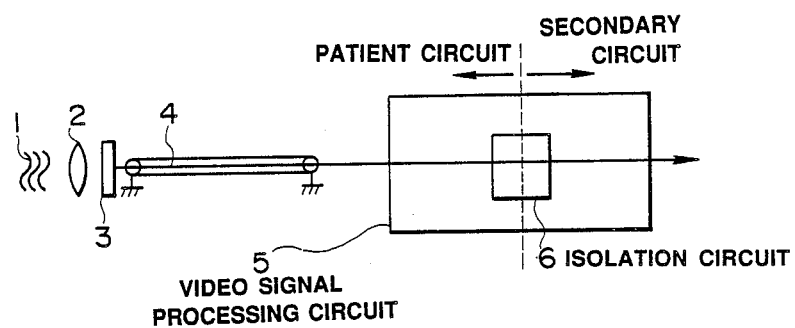
FIGS. 1 to 3 relate to the related art.
Figure 2:
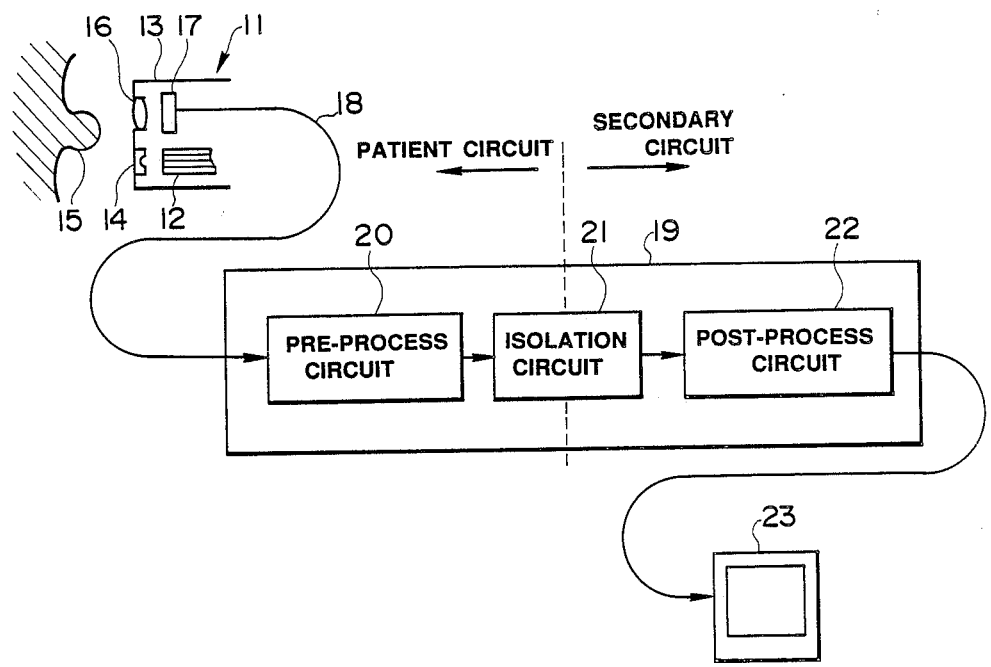
Figure 3:
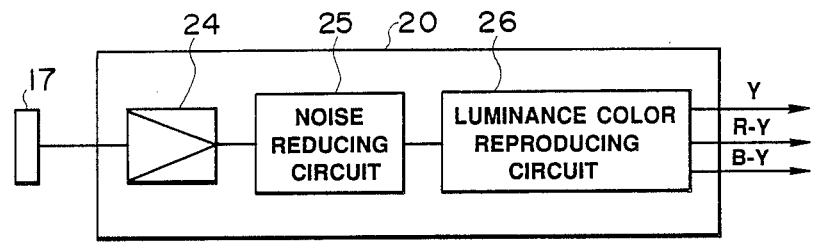
Figure 4:
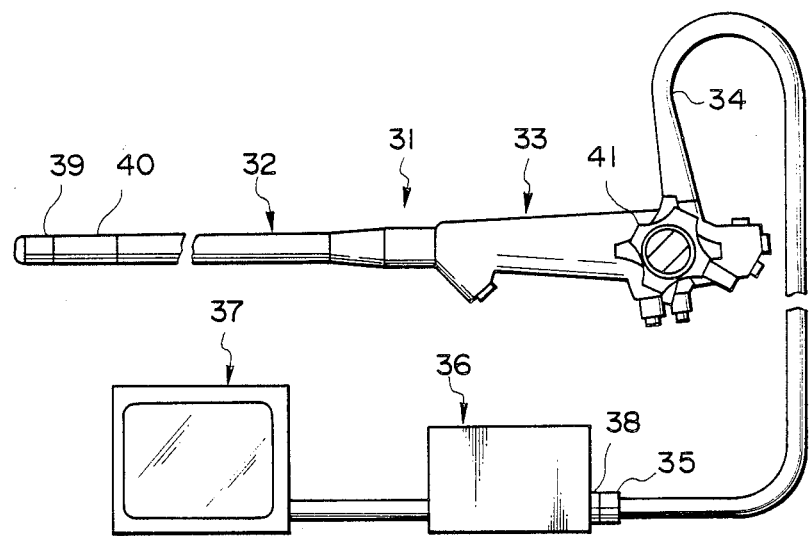
FIGS. 4 and 6 relate to the first embodiment of the present invention.
Figure 5:
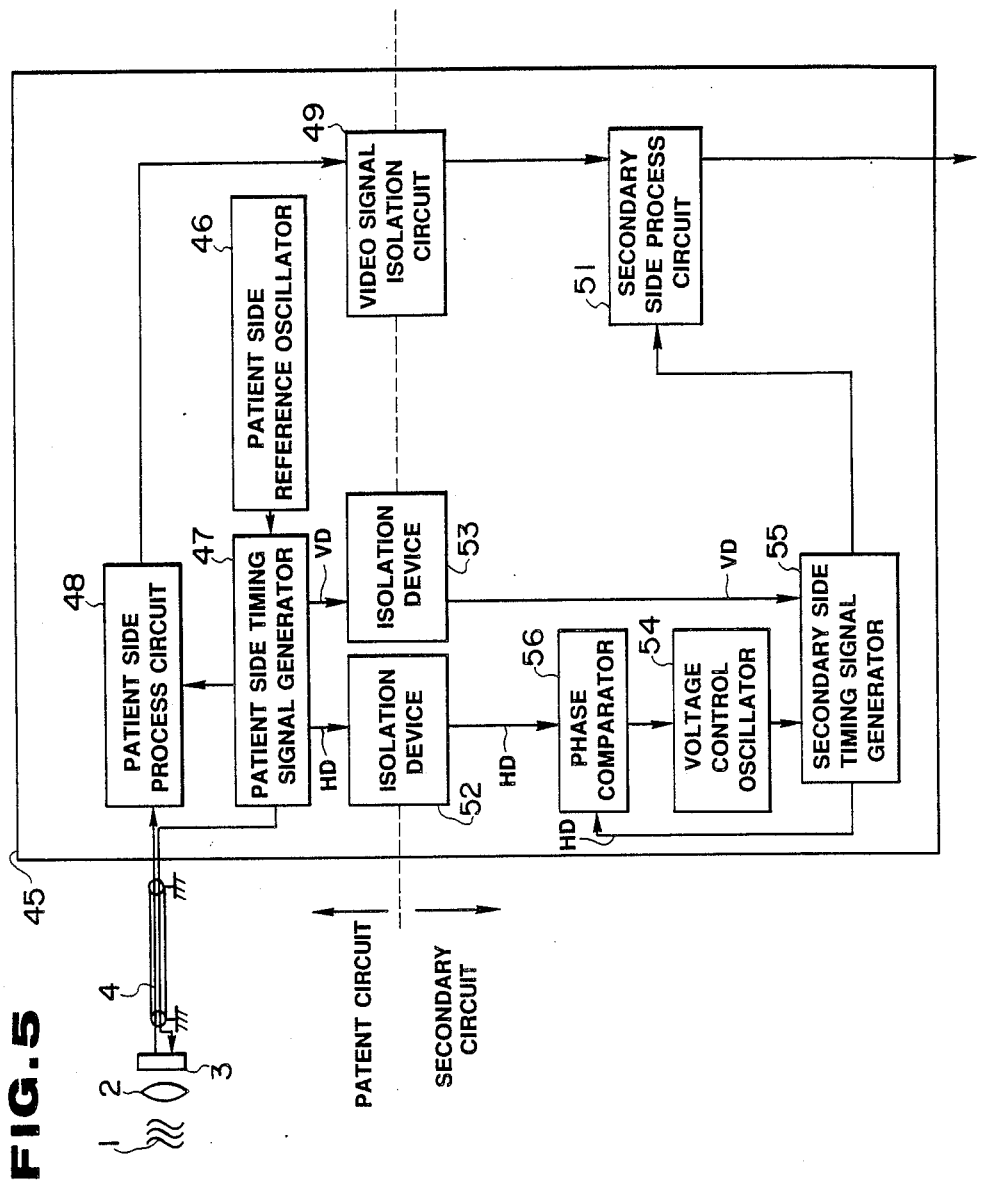
FIG. 5 is a block diagram showing the formation of an electronic endoscope apparatus.
Figure 6:
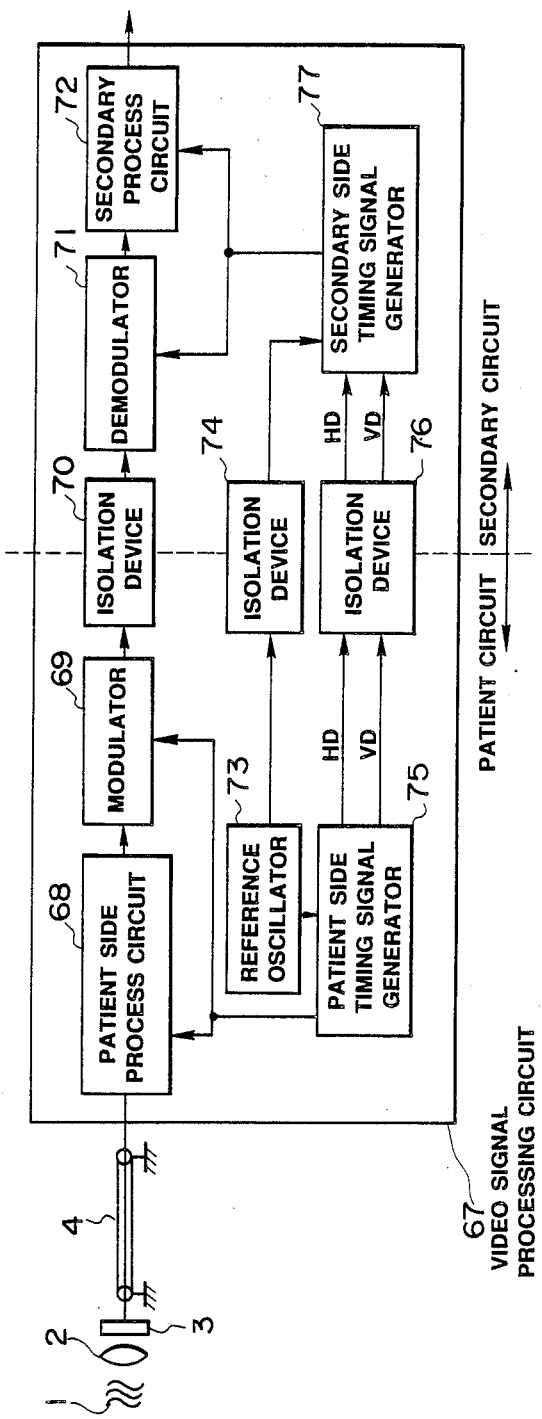

FIGS. 4 to 6 show the first embodiment of the present invention.

As shown in FIG. 4, an electronic endoscope 31 is provided with an elongate and, for example, flexible insertable part 32 and a thick operating 33 connected to the rear end of this insertable part 32.

A flexible universal cord 34 is extended sidewise from the rear end part of the above mentioned operating part 33 and is connected at the tip with a connector 35 which is connected to a connector receptacle 38 of a video processor 36 containing a light source device and video signal processing circuit (not illustrated).

A rigid tip part 39 and a curvable part 40 curvable rearward and adjacent to this tip part 39 are sequentially provided on the tip side of the above mentioned insertable part 32. The above mentioned operating part 33 is provided with a curving operation knob 41 so that, by rotating this curving operation knob 41, the above mentioned curvable part 40 may be curved in the vertical and horizontal directions. Also, the above mentioned operating part 33 is provided with an inserting port communicating with a treating instrument channel provided within the above mentioned insertable part 32.

As shown in FIG. 5, the above mentioned tip part 39 is provided with an image forming optical system 2. A solid state imaging device 3 as an imaging means is arranged in the image forming position of this image forming optical system 2. Here, the solid state imaging device 3 may be a CCD (charge coupled device) or MOS type solid state imaging device. A signal transmitting and receiving cable 4 is connected to the above mentioned solid state imaging device 3, is inserted through the above mentioned insertable part 32 and universal cord 34, is connected to the above mentioned connector 35 and is connected to a video signal processing circuit 45 contained in the above mentioned video processor 36 through this connector 35 and connector receptacle 38. In case that a simultaneous system is to be used as a color imaging system, a color filter array in which color filters respectively transmitting color light of red (R), green (G) and blue (B) are arranged in the form of a mosaic is provided on the front surface of the above mentioned solid state imaging device 3. An illuminating light emitted from a light source device (not illustrated) contained in the above mentioned video processor 36 is radiated to an object 1 through a light guide (not illustrated). In case a frame sequential system is used for the color imaging system, a light source device emitting frame sequential illuminating light of R, G and B will be used for the above mentioned light source device.

The light returning from the above mentioned object 1 is made to form an image on the solid state imaging device 3 by the image forming optical system 2. This solid state imaging device 3 is connected to the above mentioned video signal processing circuit 45 through the cable 4.

The above mentioned video signal processing circuit 45 is formed of a patient circuit and secondary circuit isolated from each other. The above mentioned patient circuit is provided with a patient side reference oscillator 46, a patient side timing signal generator 47 generating various timing pulses by reference clocks from this patient side reference oscillator 46 and a patient side process circuit 48 pre-processing the output signal of the above mentioned solid state imaging device 3. A solid state imaging device driving pulse and patient side process circuit 48 timing pulse are generated by a patient side reference clock from the above mentioned patient side timing signal generator 47. The above mentioned solid state imaging device driving pulse is transmitted to the solid state imaging device 3 through the cable 4 and a picture image signal is read out of the above mentioned solid state imaging device 3 by this driving pulse. This picture image signal is input into the above mentioned patient side process circuit 48 through the cable 4. This patient side process circuit 48 is timing controlled by the above mentioned patient side process circuit 48 and pre-processes the output signal of the above mentioned solid state imaging device 3. The video signal from this patient side process circuit 48 is transmitted from the patient circuit to the secondary circuit through a video signal isolation circuit 49.

The above mentioned secondary circuit is provided with a secondary side process circuit 51 into which the video signal transmitted to the secondary circuit through the above mentioned video signal isolation circuit 49 is input. The video signal is processed by this secondary side process circuit 51 and is output to the above mentioned monitor 37 or the like.

On the other hand, the horizontal synchronized signal (HD) and vertical synchronized signal (VD) generated from the above mentioned patient side timing signal generator 47 are transmitted to the secondary circuit through isolating devices 52 and 53 sufficient for the pressure-proofness between the patient circuit and secondary circuit such as respectively photocouplers.

On this secondary circuit side, a synchronized signal coinciding in phase with the horizontal synchronized signal (HD) and vertical synchronized signal (VD) transmitted through the above mentioned isolation devices 52 and 53 is generated by using a phase synchronizing loop (PLL). That is to say, in the secondary circuit, there are provided a voltage controlling oscillator (VOC) 54 as a secondary side reference oscillator and a secondary side timing signal generator 55 generating a horizontal synchronized signal (HD') with a reference clock from this voltage controlling oscillator 54 as a reference. Also there is provided a phase comparator 56 into which are input the horizontal synchronized signal (HD) from the patient side timing signal generator 47 and the horizontal synchronized signal (HD') from the above mentioned secondary side timing signal generator 55 transmitted through the above mentioned isolation devices 52 and 53. This phase comparator 56 compares the phases of the above mentioned horizontal synchronized signals HD and HD' and transmits a signal corresponding to the phase difference to the above mentioned voltage controlling oscillator 54. By the thus formed PLL, the frequency phases are controlled so that the phases of the patient side horizontal synchronized signal (HD) and secondary side horizontal synchronized signal (HD') may coincide with each other.

The vertical synchronized signal (VD) transmitted through the above mentioned isolating device 53 resets the above mentioned secondary side timing signal generator 55.

Thus, the phases of the patient side and secondary side horizontal and vertical synchronized signals coincide with each other and the other timing pulses are generated with the horizontal and vertical synchronized signals as references and therefore coincide with each other in timing. Synchronized signals such as the horizontal and vertical synchronized signals from the above mentioned secondary side timing signal generator 55 are transmitted to the secondary side process circuit 51.

In the secondary side process circuit 51, the video signal from the video signal isolation circuit 49 is processed from the horizontal synchronized signal and vertical synchronized signal from the secondary side timing signal generator 55, is converted to a video signal such as, for example, an NTSC or three primary color signals of R, G and B and is output to the monitor 37 in which the image of the object 1 is displayed.

In this embodiment, as shown in FIG. 6, the timing pulse is not output to the secondary circuit side through the isolating device 74 but the vertical and horizontal signals (VD and HD) are output and therefore comparatively low frequency isolating devices 52 and 53 can be used. The signal line for the timing pulse can be omitted. With the above configuration, cost can be reduced.

FIG. 6 shall be explained. The returning light from the object 1 is made to form an image on the solid state imaging device 3 by the image forming optical system 2. This solid state imaging device 3 is connected to the video signal processing circuit 67 through the cable 4. The above mentioned video signal processing circuit 67 is formed of a patient circuit and secondary circuit isolated from each other.

The patient side process circuit 68 on the above mentioned patient circuit side converts the picture image signal from the solid state imaging device 3 to a video signal. The above mentioned video signal is somewhat modulated by the modulator 69, is transmitted to the secondary circuit side through isolating device 70 such as a high frequency transformer or high speed photocoupler, is demodulated by the demodulator 71 and is processed by the secondary circuit side process circuit 72.

The timing pulse transmits the reference clock generated from the reference oscillator to the secondary side through isolating device 74 such as a high frequency transformer or high speed photocoupler. At the same time, the patient circuit side timing signal generator 75 receives the above mentioned reference clock and transmits the horizontal synchronized signal and vertical synchronized signal to such isolating device 76 as an ordinary photocoupler and various timing pulses to be used on the secondary circuit side are made by the secondary circuit side timing signal generator 77.

In this embodiment, the horizontal synchronized signal (HD) generated on the patient side and the secondary side horizontal synchronized signal (HD') are directly compared in phase on the secondary circuit side. However, instead of the secondary side horizontal synchronized signal, a pulse splitting the frequency of the voltage controlling oscillator, as the secondary side reference oscillator, so as to be the same frequency as the horizontal synchronized signal (HD') and the patient side horizontal synchronized signal (HD) are compared in phase, the voltage controlling oscillator is controlled and the resetting operation is made in the secondary timing signal with the patient side horizontal synchronized signal (HD) and vertical synchronized signal (VD) so that the phases of the patient side and secondary side horizontal and vertical synchronized signals may coincide with each other. Also, instead of the vertical synchronized signal (VD), a vertical resetting signal adapted to the secondary timing signal generator may be transmitted.

Also, in this embodiment, on the patient circuit side, there is the reference oscillator by which the voltage controlling oscillator on the secondary circuit side is controlled but, the reference oscillator may be located on the secondary circuit side to control the patient side voltage controlling oscillator.

Even in case the number of pixels of the solid state imaging device varies and the reference transmitting frequencies on the patient circuit side and secondary circuit side are different from each other, if the frequency splitting ratio is considered, the above mention configuration will be possible.

Figure 7:
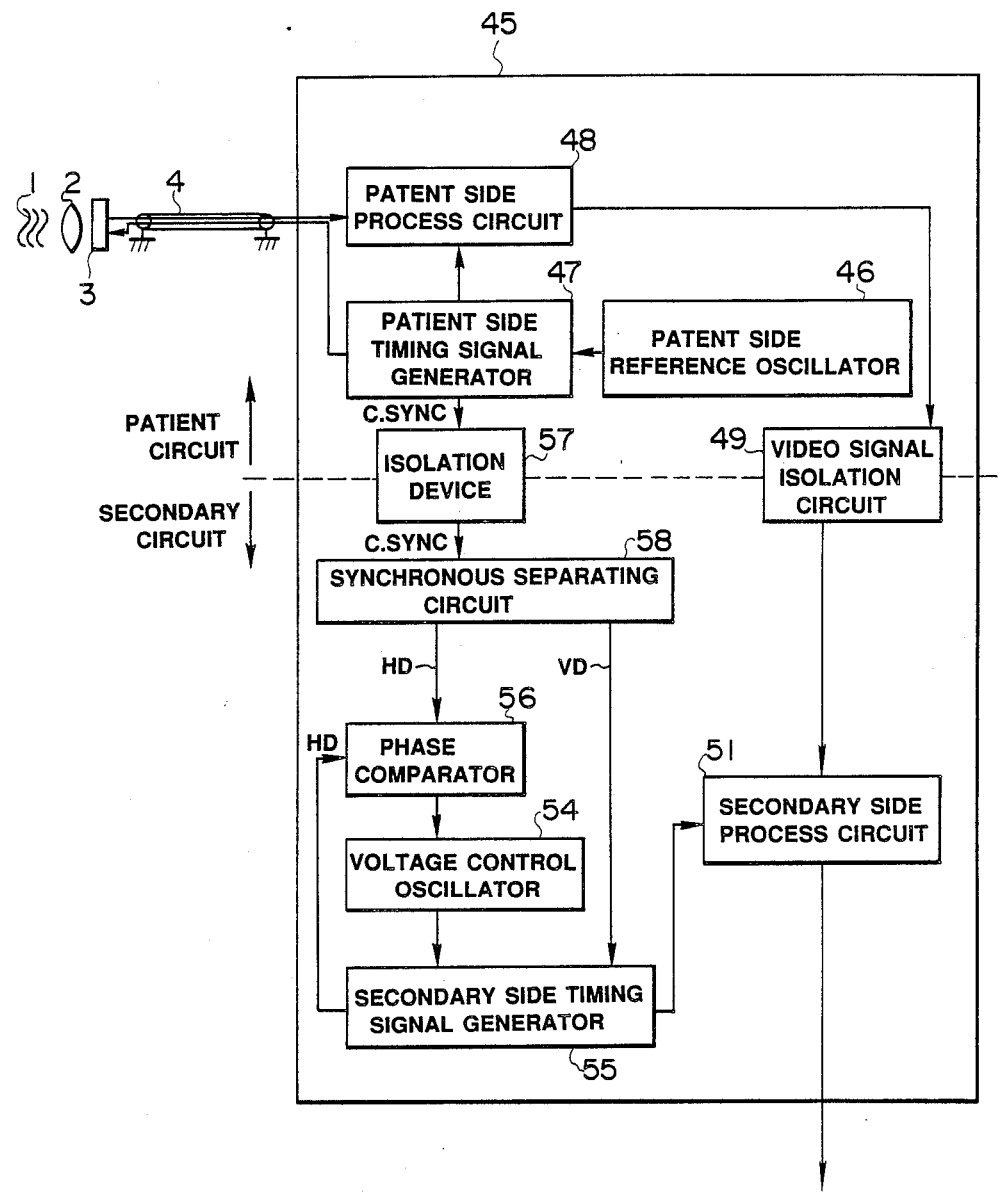
FIG. 7 relates to the second embodiment of the present invention and is a block diagram showing the formation of an electronic endoscope apparatus.

FIG. 7 shows the second embodiment of the present invention.

In FIG. 7, a composite synchronized signal is generated from the patient side timing signal generator 47 and is transmitted to the secondary circuit side through the isolation device 57. On the above mentioned secondary circuit side, the above mentioned composite synchronized signal is separated into the horizontal synchronized signal (HD) and vertical synchronized signal (VD) by the synchronized separating circuit 58. The other formations, operations and effects are the same as in the first embodiment.

According to the above mentioned first and second embodiments, the timing pulses of the patient circuit and secondary circuit can be isolated from each other by using a comparative low frequency isolating device and the number of the signal lines can be reduced.

Also, even in case the number of pixels of the solid state imaging device varies and the patient circuit side reference transmitting frequency and the secondary circuit side reference transmitting frequency are different from each other, when the patient circuit and secondary circuit are separated from each other, the interference caused by the differences in the frequencies between the patient circuit and secondary circuit may be eliminated.

Figure 8:
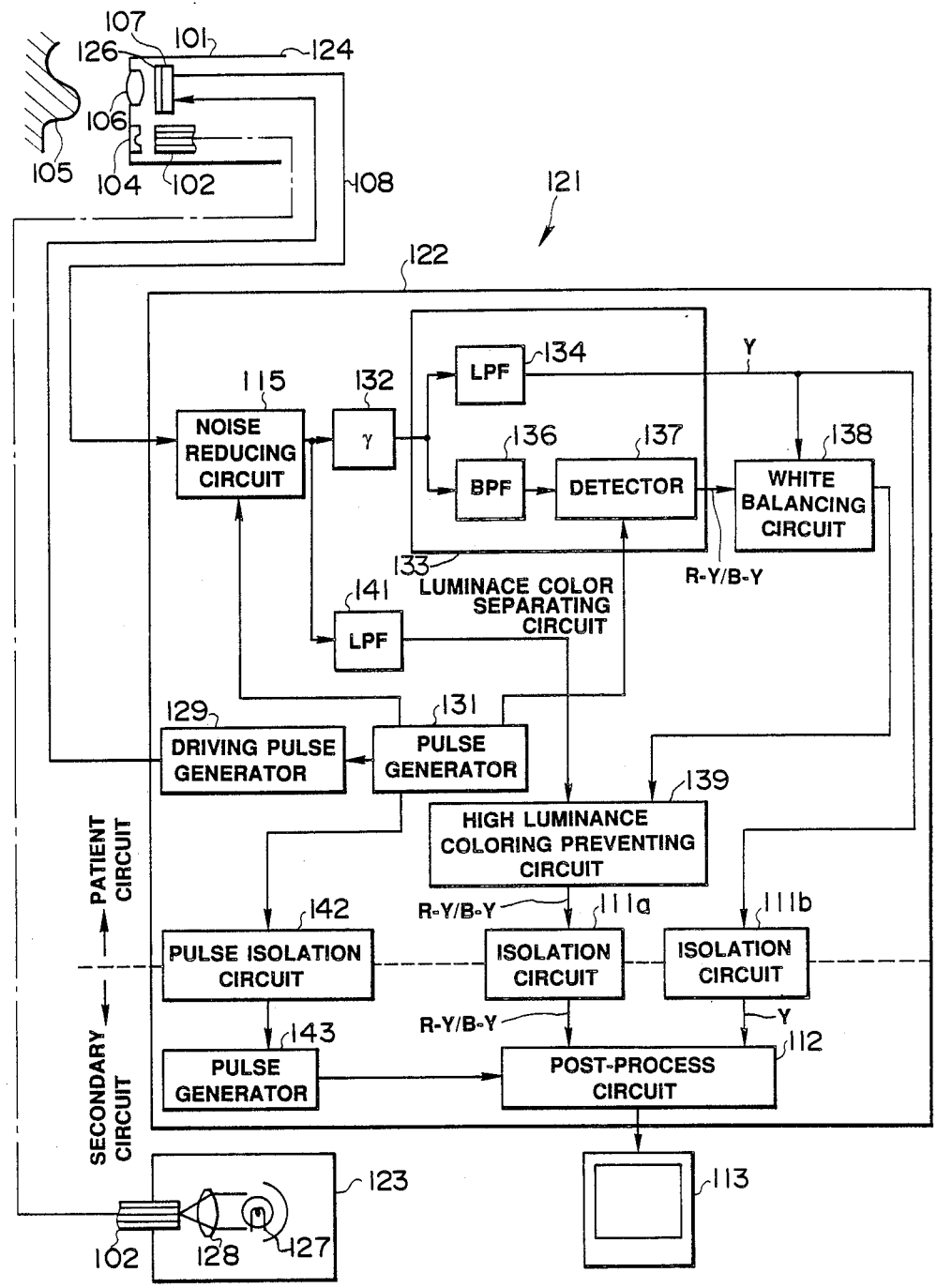
FIGS. 8 and 9 relate to the third embodiment of the present invention.
Figure 9:
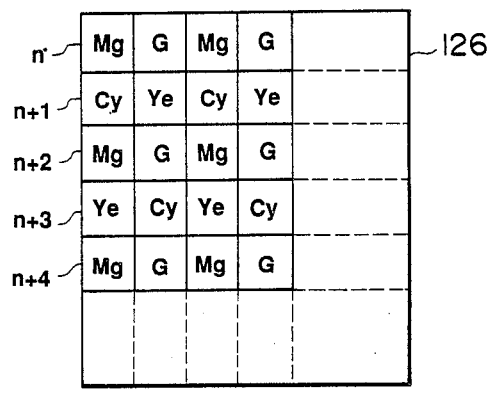

FIGS. 8 and 9 show the third embodiment of the present invention.

As shown in FIG. 8, an electronic endoscope apparatus 121 of this embodiment comprises an electronic scope 101, a camera control unit (which shall be abbreviated as CCU hereinafter) 122 connected with this electronic scope and processing signals, a light source device 123 feeding an illuminating light to the above mentioned electronic scope 101 and a color monitor 113 displaying the video signal output from the above mentioned CCU 122.

In the above mentioned electronic scope 101, an elongate insertable part 124 is formed so as to be easily insertable into a body cavity and an image forming optical system 106 is provided on the tip side of this insertable part 124. A CCD 107 as an imaging means is provided in the image forming position of this image forming optical system 106. A color filter array 26 of a supplementary color system of yellow (Ye transmitting R and G), magenta (Mg transmitting R and B) and cyan (Cy transmitting B and G) such as is shown in FIG. 9 is pasted on the imaging surface of this CCD 107.

A light guide formed of a fiber bundle transmitting an illuminating light is inserted through the above mentioned insertable part 124, transmits the illuminating light fed from the light source device 123 and emits it from the exit end surface to illuminate an object 105 through a light distributing lens system 104.

The above mentioned light source device 123 feeding the illuminating light to the hand base side end surface of the above mentioned light guide 102 comprises a light source lamp 127 and a condenser lens 128 condensing and radiating the illuminating light of this light source lamp 127 to the end surface of the light guide 102.

The object 105 image illuminated by the illuminating light is color-separated by the color filter array 126 and is formed on the imaging surface of the CCD 107 by the image forming optical system 106. The object 105 image formed on the imaging surface of the CCD 107 is photoelectrically converted and is read out as an electric signal by applying a driving pulse from a driving pulse generator 129. The driving pulse generator 129 receives the pulse signal from the pulse generator 131 and generates a driving pulse. The electric signal including this read-out video information is input into a noise reducing circuit 115 such as, for example, a correlated double sampling circuit within the CCD 122 by a signal transmitting cable 108 inserted through the insertable part 124. The noise reducing circuit 115 makes a double sampling by a sampling pulse output from a pulse generator 131 and makes a signal improved in S/N. This signal is branched and one branch is set at the optimum $\gamma$ value and is input into a luminance color separating circuit 133 as a color signal reproducing means. In case this input signal is an output of the CCD 107 having the color filter 126, it will be in a signal form in which a color signal is multiplexed on the luminance signal Y. Within the luminance color separating circuit 133, the luminance signal Y is separated and output by a low pass filter (which shall be abbreviated as LPF hereinafter) 134. The signal input into the luminance color separating circuit 133 has simultaneously the color component separated by a band pass filter (which shall be abbreviated as BPF hereinafter) 136, is input into a detector 137 and is demodulated by a color demodulating pulse output from the pulse generator 131.

In case the color filter array 126 is of an arrangement as in FIG. 9, the color signal output from the above mentioned detector 137 will be a signal equivalent to a color difference signal such as $R-Y$ or $B-Y$ as made sequential for each horizontal line period. That is to say, in FIG. 9, two lines are simultaneously read out for one line. In the odd number fields, the n and N+1 lines in FIG. 9 are read out simultaneously and the vertical pixel information is output as mixed. In the even number fields, the n+1 and n+2 lines in FIG. 9 are read out simultaneously and the vertical pixel information is output as mixed. The odd number fields shall be explained. In the line in which the n and n+1 lines are mixed, the signal of the addition of respective pixels, that is, $$Mg + Cy + G + Ye$$
$$= R + B + B + G + G + R + G$$
$$= 2R + 3G + 2B$$

will be equivalently a luminance signal Y and the signal obtained by subtracting the adjacent pixels, that is, $$(Mg + Cy) - (G + Ye)$$
$$= (R + B + B + G) - (G + R + G)$$
$$= 2B - G$$

will be equivalently a color difference signal $B-Y$.

In the line in which the n+2 and n+3 lines are mixed, the signal of the addition of respective pixels will be $$Mg + Cy + G + Ye$$
$$= R + B + B + G + G + R + G$$
$$= 2R + 3G + 2B$$

and will be equivalently a luminance signal Y the same as in the above mentioned line in which the n and n+1 lines are mixed and the signal obtained by subtracting the adjacent pixels, that is, $$(Mg + Ye) - (G + Cy)$$
$$= (R + B + R + G) - (G + B + G)$$
$$= 2R - G$$

will be equivalently a color difference signal $R-Y$.

The luminance color separating circuit 133 may be a sampling circuit.

The color difference signals R−Y and B−Y output from the luminance color separating circuit 133 are made sequential in a white balancing circuit 138 and are adjusted in white balance. The color difference signals R−Y and B−Y output from this white balancing circuit are delivered to a high luminance coloring preventing circuit 139. In this high luminance coloring preventing circuit 139, as the color filter array 126 is pasted on to the CCD 107 and the luminance levels saturated by the pixels for the respective colors are different, so that the white balance may not be broken and no coloring may be produced, the color signal component is removed from the output signal not γ-corrected of the noise reducing circuit 115 by the LPF 141 and the color difference signal level of the part in which the level becomes large by the signal from which the color signal component is removed and the white balance of the color difference signal is broken is attenuated. The color difference signal R−Y/B−Y made sequential and output from this high luminance coloring preventing circuit 139 is input into an isolation circuit as, for example, a transformer, is transmitted from the patient circuit to the secondary circuit and is input into the post-process circuit 112 as a video signal processing means. The luminance signal Y separated by the LPF 134 is input into the isolation circuit 116b, is then input into the post-process circuit 112 and is processed as determined together with the color difference signals R−Y and B−Y. The isolation circuits 111a and 111b isolate the patient circuit in the forward steps and the secondary circuit in the rearward steps from this.

On the other hand, a secondary circuit timing pulse is generated from the patient circuit side pulse generator 131, is delivered to the secondary circuit side by the pulse circuit side pulse generator 142, is input into the secondary circuit side pulse generator 143 and synchronizes various timing pulses on the patient circuit side and secondary circuit side.

The sequentialized color difference signal R−Y/B−Y input into the above mentioned post-process circuit 112 is synchronized in the synchronizing circuit (not illustrated) by the timing pulse from the pulse generator 143, is variously processed together with the luminance signal Y, is converted to a video signal as, for example, an NTSC or three primary color signals of R, G and B and is output to the color monitor 113 which displays the object 105 image.

In the above mentioned embodiment, the color difference signals R−Y and B−Y are made sequential and are input into the isolation circuit 111a and, therefore, as compared with the case of separately inputting the color difference signals R−Y and B−Y, one isolation circuit can be eliminated and the number of lines can be deceased.

Figure 10:
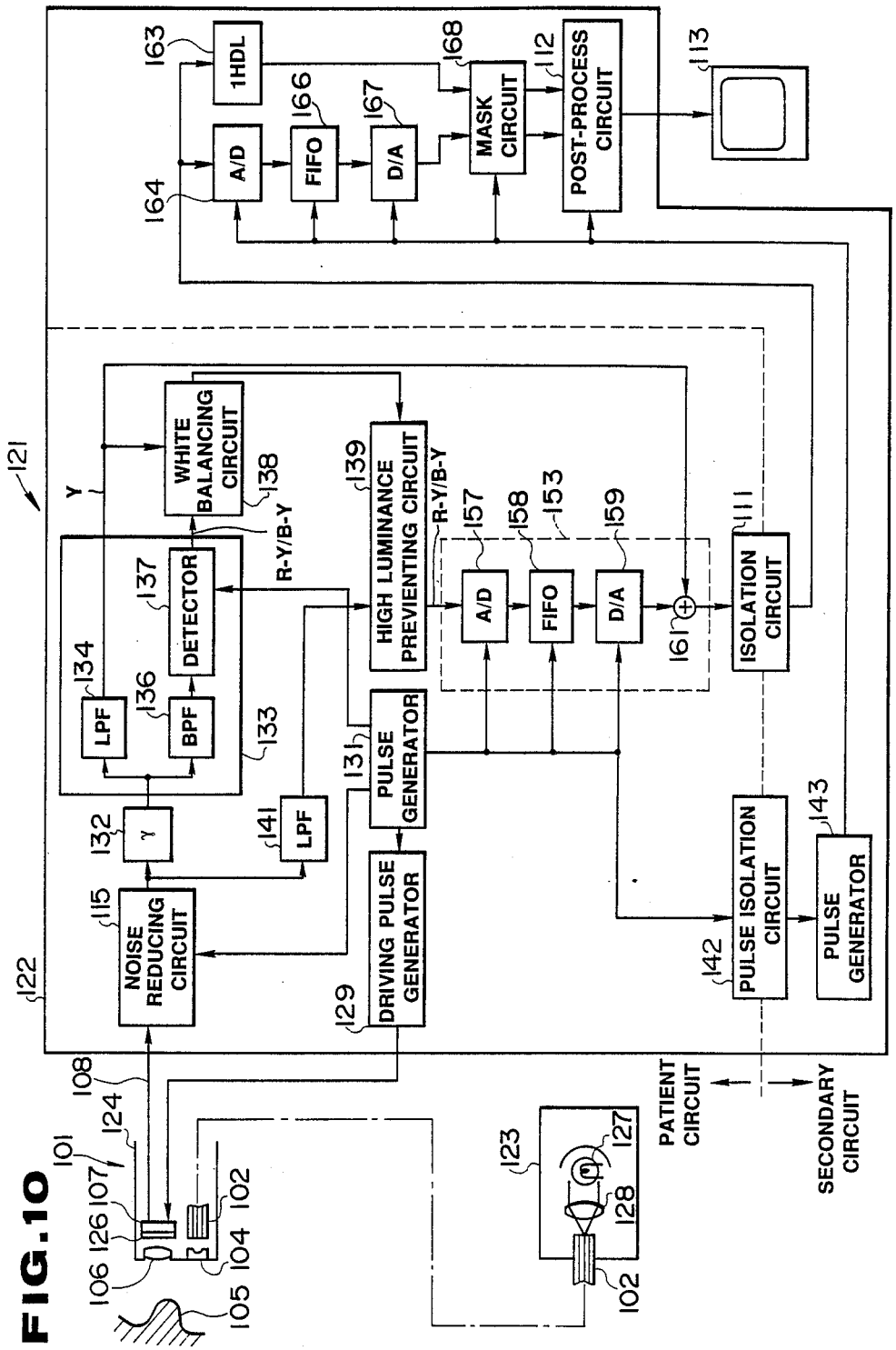
FIGS. 10 to 12 relate to the fourth embodiment of the present invention.
Figure 11:
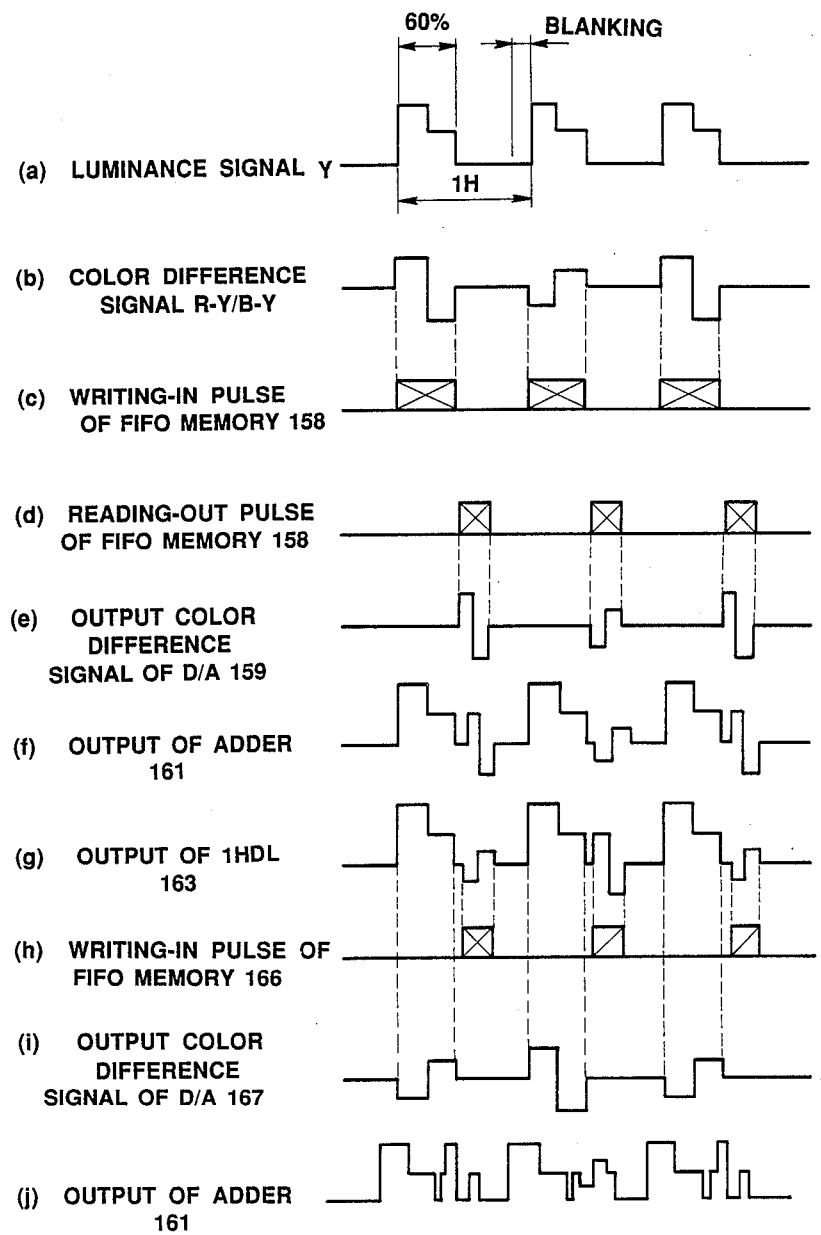
Figure 12:
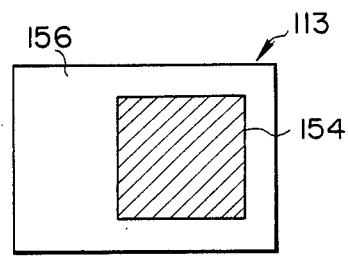

FIGS. 10 to 12 show the fourth embodiment of the present invention.

In this embodiment, the color difference signals and luminance signal are made sequential by a sequentializing means and the isolation circuit 111 is made into one circuit. In this embodiment, the formation of the steps before the high luminance coloring preventing circuit 139 is the same as in the third embodiment and shall not be explained here.

In FIG. 10, the sequentialized color difference signal R−Y/B−Y output from the high luminance coloring preventing circuit 139 is input into a sequentializing means 153.

In the electronic endoscope, a small type of solid state imaging device is used and, in order to display various data on one picture surface, the displayed picture image 154 displaying the endoscope image is a part of the displayed picture surface 156 of the monitor 113 as shown in FIG. 12. For example, if the luminance signal Y output by the luminance color separating circuit 133 and the sequentialized color difference signal R−Y/B−Y output by the high luminance coloring preventing circuit 139 are represented by H rates, they will be as shown, for example, in FIGS. 11(a) and (b). This picture image output period is usually about 60% of the 1H period less the blanking period.

Returning to FIG. 10, the sequentialized color difference signal R−Y/B−Y output by the high luminance coloring preventing circuit 139 is converted into a digital signal by the A/D converter 157. The color difference signal R−Y/B−Y converted into this digital signal is input into an FIFO (first in first out) memory 158 which can be read out the input data at any timing. The input and output timings of this FIFO memory 158 are shown in FIGS. 11(c), (d) and (e). FIG. 11(c) shows the timing of the writing-in pulse of the FIFO memory 158. FIG. 11(d) shows the timing of the reading-out pulse of this FIFO memory 158. FIG. 11(e) shows the color difference signal output by the FIFO memory 158. The digitalized color difference signal R−Y/B−Y is input into the FIFO memory 158 sequentially in time from the writing-in pulse. At the time point when the picture image output period ends, the signal will be read out by the reading-out pulse at a speed twice as high as writing in. The read-out output signal of the FIFO memory 158 will be a digital signal of the waveform shown in FIG. 11(e). When this signal is returned to an analogue signal by the D/A converter 159 and is added to the above mentioned luminance signal Y by the adder 161, as shown in FIG. 11(f), a waveform will be made in which the color difference signal R−Y/B−Y is inserted in the other non-signal period than the picture image output period of the luminance signal.

The above mentioned sequentializing means 153 comprises the A/D converter 157, FIFO memory 158, D/A converter 159 and adder 161.

The added luminance signal and color difference synchronizing signal are input into an isolation circuit 111 as, for example, a transformer. The patient circuit in the steps before this isolation circuit 111 and the secondary circuit in the later steps are isolated from each other.

Here, the color difference signal R−Y/B−Y is read out at a speed twice as high as in writing in and is therefore of a band twice as large as the band of the color difference signal before the A/D conversion. However, the band of the color difference signal R−Y/B−Y is 5 to 1 MH$_2$ and is about ¼ of the luminance signal band, therefore the output of the adder 161 is below the luminance signal band and the isolation circuit 111 can transmit the signal to the secondary circuit side.

On the secondary circuit side, the luminance and color difference sequentialized signals are branched, one branch is 1H-delayed by the 1H delay line 163 and the other is digitalized again by the A/D converter 164. The digitalized signal is input into the FIFO memory 166. In this FIFO memory 166, only the color difference signal is written in at the timing in FIG. 11(h) and is read out as in FIG. 11(i) at a speed ½ the writing in at the timing of the luminance signal of the 1H delay line 163. This output signal of the FIFO memory 166 is converted to an analogue signal by the D/A converter and is input into the masking circuit 168 together with the output signal of the 1H delay line. In the masking circuit 168, the color difference component contained in the signal from the 1H delay line 163 is removed and the components other than the effective picture image part are masked. The signal from the masking circuit 168 is input into the post-process circuit 112. This signal is a signal equivalent to the luminance signal Y which is an output of the luminance color separating circuit in the patient circuit and the color difference signal R−Y/B−Y which is an output of the high luminance coloring preventing circuit 139.

On the other hand, a secondary circuit timing pulse is generated from the pulse generator 131 on the patient circuit side, is also delivered to the secondary circuit side by the pulse isolation circuit 142 and is input into the pulse generator 143 on the secondary side and a timing pulse synchronized with the patient circuit side is input into the A/D converter 164, FIFO memory 166, D/A converter 167, masking circuit 168 and post-process circuit 112.

The data input into the above mentioned post-process circuit 112 is synchronized in a synchronizing circuit (not illustrated) by a timing pulse from the pulse generator 143, are variously processed together with the luminance signal Y, are converted to a video signal as, for example, an NTSC or three primary color signals of R, G and B and are output to the color monitor 113 which displays the image of the object 105.

In the above mentioned embodiment, since the color difference signals R−Y and B−Y are inserted in the non-signal period other than the picture image outputting period of the luminance signal Y, the signal transmitting path can be made into one path and further thereby the signal isolation circuit for the luminance signal and color difference signals can be made into one circuit.

Figure 13:
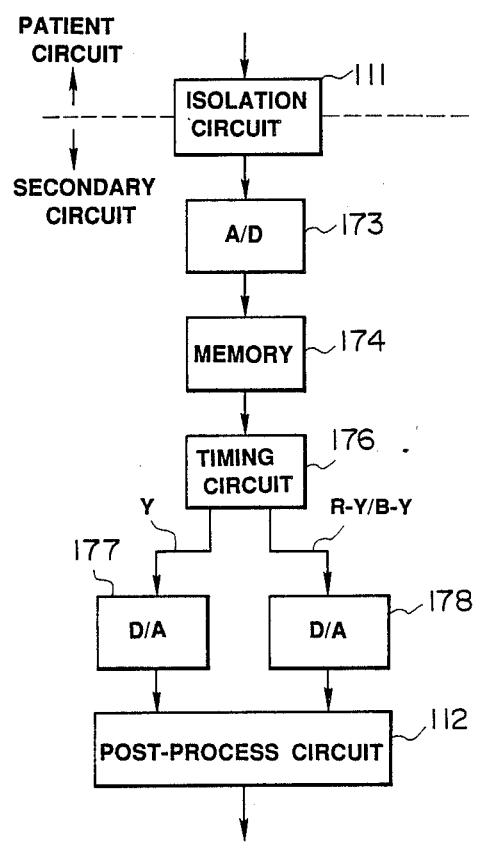
FIG. 13 is a block diagram showing a modification of the fourth embodiment.

FIG. 13 is a block diagram showing a modification of the fourth embodiment.

In this modification, a video signal recording picture image memory is provided on the secondary circuit side.

In FIG. 13, the steps before the isolation circuit 111 are the same as of the fourth embodiment. The luminance and color difference synchronized signal transmitted by the isolation circuit 111 is converted to a digital signal by the A/D converter 173. This digital signal is input and stored in the picture image memory 174. In this case, as shown in FIG. 11(f), as the luminance signal and color difference signals are present within the 1H period, the picture image memory will operate the same as a frame memory or field memory usually storing the luminance signal and color difference signals to be able to store the luminance signal and color difference signals. Therefore, the memory usually requiring the two systems of the luminance system and color difference system can be made to require one system. Also, since the memory drive is of only one system, the circuit is simplified. The signal read out of this picture image memory 174 is digitally timed with the luminance signal and color difference signals the same as in the fourth embodiment by the timing circuit 176, is converted to an analogue signal by the D/A converters 177 and 178, is input into the post-process circuit 112, is processed as determined and is output. In this case, as in FIG. 11(j), by the dynamic range relation of the picture image memory 174, the color difference signal may be set up, for example, in the adder 161 and may be stored.

Figure 15:
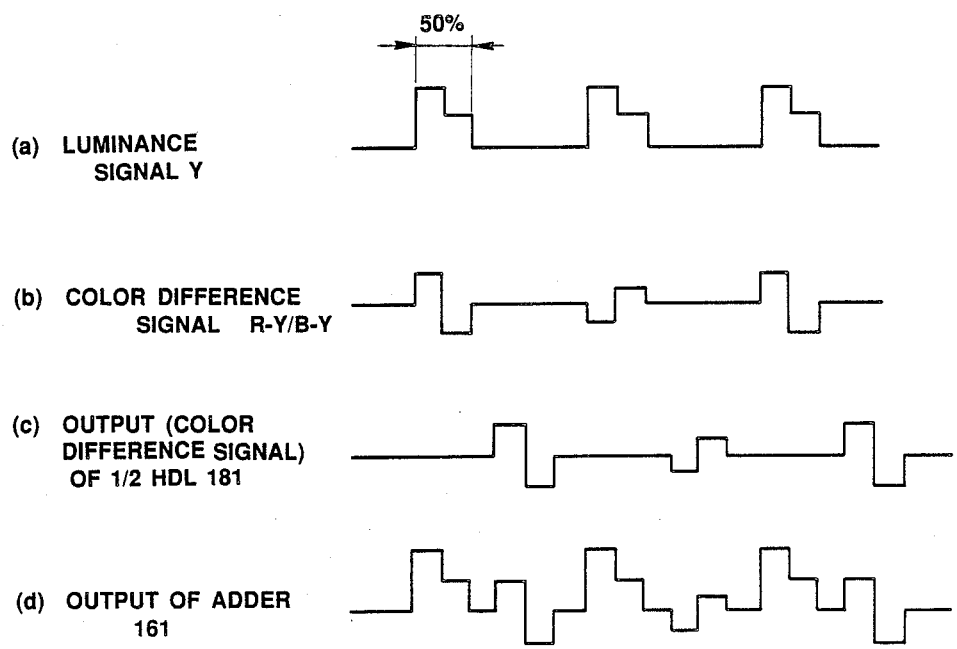

FIGS. 14 and 15 show the fifth embodiment of the present invention.

This embodiment is when the output picture image signal period of the CCD 107 is below 50% of the 1H period less the blanking period.

In this embodiment, the formation of the steps before the high luminance coloring preventing circuit 139 is the same as in the fourth embodiment and the same operating components are fitted with the same reference numerals and are not explained here.

The color difference signal R−Y/B−Y output from the high luminance coloring preventing circuit 139 and shown in FIG. 15(b) is input into the ½ H delay line 181 and is delayed by ½ H. This delayed color diffrence signal R−Y/B−Y is added by the adder 161 to the luminance signal Y in FIG. 15(a) output from the luminance color separating circuit 133 to be a luminance and color difference sequential signal which is shown in FIG. 15(d), is input into the isolation circuit 111 and is transmitted to the secondary circuit side.

In this embodiment, the sequentializing means 153 is formed of the ½ H delay line 181 and adder 161.

On the secondary circuit side, a luminance and color difference sequential signal as is shown in FIG. 15(d) is input into the 1H delay line 182 and ½ H delay line 183. The output of the 1H delay line 182 is the luminance signal of the normal timing and the output of the ½ H delay line 183 is the color difference signal of the normal timing. These signals have the unnecessary parts masked by the masking circuit 168, are input into the post-process circuit 112 and are processed as determined.

With such a formation as in the above, the luminance signal and color difference signal can be easily made sequential and the isolation circuit and circuit can be simplified.

In this embodiment, as the output picture image signal period of the CCD 107 is below 50% of the 1H period less the blanking period, it is not necessary to compress the color difference signal as in the fourth embodiment and a cheap ½ H delay line can be used. Therefore, the cost can be further reduced.

The above mentioned respective embodiments have been explained merely on the isolation circuit and internal recording circuit but can be easily applied to any other transmitting and storing systems.

Also, in this embodiment the CCD having the color filter array of a filter arrangement as is shown in FIG. 9 has been explained but a solid state imaging device of an X−Y address system such as a MOS type imaging device may be used. In such a case, as the respective pixel outputs are independently obtained in the base band, the luminance color separating circuit will be a matrix circuit in which the respective colors are timed and then operated. In this case, too, the luminance color separating circuit output will be the luminance signal and sequential color difference signal and the later processing system will be the same as in this embodiment.

Further, the filter arrangement of the color filter array is not limited to the one in FIG. 9 but may be any color filter array having a filter arrangement in which the color signal is output as a sequentialized signal.

As explained above, according to the present invention, within the patient circuit, when the color difference signal is sequentialized and is input into the isolation circuit, the circuit will be simplified, the number of the signal lines and parts can be reduced, the color can be positively demodulated and therefore the picture quality can be improved at a low cost.

What is claimed is:

1. An electronic endoscope apparatus having an isolation circuit comprising:
   an endoscope provided with an imaging means converting the photoinformation of an object into an output electric signal;
   a video signal processing means processing the output electric signal of said imaging means into a video signal;
   an isolating means for separating and for isolating said video signal processing means into a) a patient circuit including said imaging means and b) a secondary circuit which is a circuit not included in said patent circuit; and
   a signal producing means for making either one of said patient circuit and said secondary circuit a transmitted side circuit and the other a transmitting side circuit and for producing a signal required by said transmitted side circuit based upon a signal forming an image transmitted to the transmitted side circuit through said isolating means from the transmitting side circuit.

2. An electronic endoscope apparatus having an isolation circuit according to claim 1 wherein said signal forming the image is at least either one of a synchronized signal and video signal.

3. An electronic endoscope apparatus having an isolation circuit according to claim 1 wherein said transmitting circuit has a reference clock oscillator producing a reference clock and a timing signal generator generating at least a horizontal synchronized signal and vertical synchronized signal from said reference clock.

4. An electronic endoscope apparatus having an isolation circuit according to claim 3 wherein said isolating means isolates said vertical synchronized signal and horizontal synchronized signal and transmits said vertical and horizontal synchronized signals to said transmitted side circuit.

5. An electronic endoscope apparatus having an isolation circuit according to claim 3 wherein said signal producing means has a phase synchronizing circuit to which said vertical synchronized signal and horizontal synchronized signal isolated from each other by said isolating means are input, a phase of said vertical synchronized signal is synchronized and a synchronized signal synchronized in said phase is output.

6. An electronic endoscope apparatus having an isolation circuit according to claim 1 wherein said transmitted side circuit has a reference clock oscillator producing a reference clock and a timing signal generator generating at least a composite synchronized signal from said reference clock.

7. An electronic endoscope apparatus having an isolation circuit according to claim 6 wherein said isolating means isolates said composite synchronized signal and transmits said to said transmitted side circuit.

8. An electronic endoscope apparatus having an isolation circuit according to claim 6 wherein said signal producing means has a synchronization signal separator circuit in which the vertical synchronized signal and horizontal synchronized signal are separated from said composite synchronized signal isolated by said isolating means and a phase synchronizing circuit to which said vertical synchronized signal and horizontal synchronized signal separated by said synchronization signal separator circuit are input, a phase of said vertical synchronized signal is synchronized and the synchronized signal synchronized in said phase is output.

9. An electronic endoscope apparatus having an isolation circuit according to claim 5 or 8 wherein said phase synchronizing circuit comprises a voltage controlling oscillator as a secondary side reference oscillator, a secondary side timing signal generator generating at least a horizontal synchronized signal based upon the reference clock from said voltage controlling oscillator and a phase comparator comparing the phases of the horizontal synchronized signal from said isolating means and the horizontal synchronized signal of said secondary side timing signal generator.

10. An electronic endoscope apparatus having an isolation circuit according to claim 5 and 8 wherein said signal producing means further has a secondary side process circuit producing said video signal based upon the synchronized signal from said phase synchronizing circuit.

11. An electronic endoscope apparatus having an isolation circuit according to claim 1 wherein said transmitting side circuit has a sequentializing circuit sequentializing a color difference signal.

12. An electronic endoscope apparatus having an isolation circuit according to claim 11 wherein said isolating means isolates said sequentialized color difference signal and a luminance signal.

13. An electronic endoscope apparatus having an isolation circuit according to claim 12 wherein said signal producing means has a secondary side process circuit producing said video signal from the color difference signal and the luminance signal from said isolating means.

14. An electronic endoscope apparatus having an isolation circuit according to claim 1 wherein said transmitting side circuit has a sequentializing circuit sequentializing a color difference signal and a superimposing circuit superimposing said sequentialized color difference signal and a luminance signal.

15. An electronic endoscope apparatus having an isolation circuit according to claim 14 wherein said isolating means isolates said superimposed color difference signal and said luminance signal.

16. An electronic endoscope apparatus having an isolation circuit according to claim 15 wherein said signal producing means has a separating means separating a color difference signal and a luminance signal from the signal from said isolating means.

17. An electronic endoscope apparatus having an isolation circuit according to claim 16 wherein said signal producing means further has a secondary side process circuit producing a video signal from said separated color difference signal and said luminance signal.

* * * * *